United States Patent [19]

Lacy et al.

[11] Patent Number: 5,079,160
[45] Date of Patent: Jan. 7, 1992

[54] METHOD TO ISOLATE CLUSTERS OF CELL SUBTYPES FROM ORGANS

[76] Inventors: Paul E. Lacy, 63 Marshall Pl., St. Louis, Mo. 63119; David W. Scharp, 1469 Willow Brook Cove, St. Louis, Mo. 63146; Camillo Ricordi, Corso Porta Nuova 10, 20121 Milano, Italy

[21] Appl. No.: 59,125

[22] Filed: Jun. 8, 1987

[51] Int. Cl.$^5$ ............ C12N 5/00; C07G 15/00; A01N 1/02; C12M 1/00
[52] U.S. Cl. ................ 435/240.2; 435/240.1; 435/268; 435/240.21; 435/283; 435/287
[58] Field of Search ............ 435/283, 287, 240.1, 435/240.2, 240.25, 240.23, 71, 268

[56] References Cited

U.S. PATENT DOCUMENTS

| | | | |
|---|---|---|---|
| 4,225,671 | 9/1980 | Puchinger et al. | 435/71 |
| 4,439,521 | 3/1984 | Archer et al. | 435/240.23 |
| 4,797,213 | 1/1989 | Parisius et al. | 210/651 |

FOREIGN PATENT DOCUMENTS

| | | | |
|---|---|---|---|
| 0191613 | 8/1986 | European Pat. Off. | 435/240.21 |
| 158796 | 2/1983 | Fed. Rep. of Germany | 435/240.21 |

OTHER PUBLICATIONS

*Methods in Enzymology*, vol. LVIII, Jakoby & Pastan eds., pp. 119–131 and 257, 1979, Academic Press, N.Y.
*Tissue Culture*, Kruse & Patterson eds., pp. 298–302, 1973, Academic Press, N.Y.
Lacy et al., (1967), *Diabetes* 16:35–39.
Gray et al., (1984), *Diabetes* 33:1055–1061.
Scharp et al., (1975) *Surgery* 77:100–105.
Scharp et al., in *Methods in Diabetes Research* (1985), vol. 1, pp. 225–243, John Wiley & Son.
Kneteman et al., (1986), *Transplantation Proceedings* 18:182–185.
Horaguchi et al., (1981) *Diabetes* 30:455–458.
Kuhn et al., (1985) *Biomed. Biochim. Acta* 44:149–153.
Lacy et al., (1982) *Diabetes* 31:109–111.
Scharp et al., in an abstract presented at American Diabetes Meeting (Baltimore, Jun. 1985).

*Primary Examiner*—Elizabeth C. Weimar
*Assistant Examiner*—Gail Poulos
*Attorney, Agent, or Firm*—Flehr, Hohbach, Test, Albritton & Herbert

[57] ABSTRACT

A method to obtain purified, well-defined cell populations from intact organs uses digestion of the distended organ with suitable proteolytic enzymes and harvest of the cell subpopulation by screening the effluent from treatment of the organ with physiologically compatible medium by a filtration screen permitting the passage of the desired cells or clusters of cells, but preventing the passage of larger particles. In this manner, physical/mechanical disruption of the cell population is unnecessary, and the cells or clusters are eased out of their structural matrix and harvested directly. Application of this method to the preparation of purified Islets of Langerhans from intact pancreas is described.

20 Claims, 3 Drawing Sheets

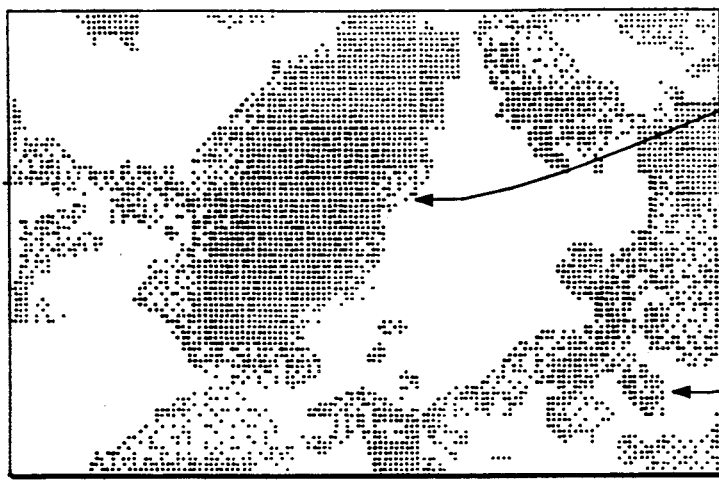
FIG.—3A
FIG.—3B
(HIGH MAGNIFICATION)
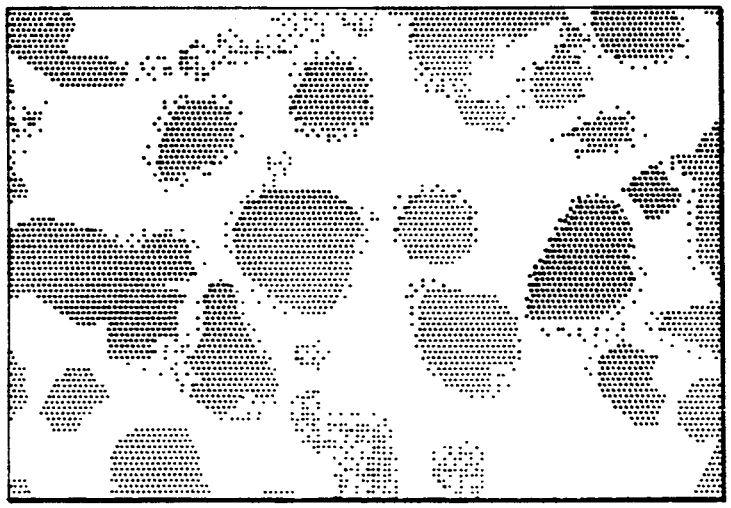
FIG.—3C
(LOW MAGNIFICATION)

METHOD TO ISOLATE CLUSTERS OF CELL SUBTYPES FROM ORGANS

TECHNICAL FIELD

The invention relates to the isolation of subpopulations of cells from organs of animals, birds, and other vertebrates. In particular, in one embodiment, it is directed to a method and apparatus for obtaining intact Islets of Langerhans from mammalian pancreatic tissue.

BACKGROUND ART

Isolation of individual cell populations from their parent organs such as liver, spleen, kidney, adrenals, and pancreas has been most intensely studied with respect to isolation of intact islets of Langerhans from the pancreas. A number of attempts have been made to obtain preparations of islets which can be used for transplantation into subjects, such as diabetics, whose own islets are not effectively functioning to secrete insulin. Isolation of, and injection of, the islets is, of course, highly preferable to whole organ transplantation. In addition to the obvious advantage of eliminating the 98-99% of the pancreas that is not required and can only cause complications, the individual islets can be more effectively preserved using low temperature and can be more effectively encapsulated, if desired, in order to minimize immune response.

Islets were first isolated from rodent pancreas by Lacy, P.E., et al, *Diabetes* (1967) 16:35-39. This method involved the use of collagenase, and the procedure was applied to the isolation of islets from human tissue by Gray, D.W.R., et al, *Diabetes* (1984) 33:1055-1061. In the Gray procedure, the tissue in the collagenase digestion mixture was further disrupted by aspiration through different sized needles. An earlier adaptation to human tissue was reported by Sharp, D.W., et al, *Surgery* (1975) 77:100-105, and this also involved physical disruption of the tissue. A method generic to mammalian pancreatic tissue which utilizes chopping or grinding of the partially digested pancreatic tissue before size separation by screening was described by Scharp, D.W., et al, *Methods in Diabetes Research* (1985), Vol. 1, Part C, pp. 225-243, John Wiley & Son.

More recently, Kneteman, N.M., et al, *Transplantation Proceedings* (1986) 18:182-185, described a method for perfusing human pancreas with a collagenase solution via the pancreatic duct, similar to the method developed by Horaguchi, A., et al, *Diabetes* (1981) 30:455-458. Subsequent treatment also involved disruption of the tissue. Kuhn, F., et al, *Biomed Biochim Acta* (1985) 44:149-153, while adopting the collagenase perfusion method employing the pancreatic duct, utilized Velcro strips in the digestion tube (duct) in order to retain the partially digested islet-containing tissue in a method adapted from that reported for the isolation of beef islets by Lacy, P.E., et al, *Diabetes* (1982) 31:109-111. Scharp, D.W., et al, in an abstract presented at American Diabetes meeting (Baltimore, June 1985) disclose a method for isolating human islets in which a collagenase solution injected into the pancreas was caused to distend the organ. The digested pancreas was passed then through a tissue macerator and size-segregated by screening.

All of the foregoing methods result in islet preparations which are useful, but which could be improved upon in terms of the quality of the islets obtained, as well as their purity. Possibly because these methods involve rather severe mechanical disruption of the tissue, the islets also become disrupted, and therefore less effective in secreting insulin. It has been calculated that one islet with a diameter of 350 microns contains more insulin-producing cells than 100 islets with an average diameter of 75 microns. Thus, more than 100 islets of the smaller size are needed for every individual islet of the larger diameter.

It would therefore be useful to provide a means to obtain islets of large diameter and high purity. These islets could then be more effectively stored, encapsulated, and transplanted to alleviate the symptomology associated with low insulin secretion. Similar considerations apply to preparation of liver cells, spleen cells, and so forth, for transplantation in connection with the relevant disorder.

DISCLOSURE OF THE INVENTION

The invention provides a method whereby the preparation of undisrupted clusters of cell subpopulations in pure form can be achieved. The method is particularly useful for the production of pure preparations of Islets of Langerhans having the individual islets retained in native form. The method employs no severe mechanical disruption of the tissue, such as chopping, grinding, extrusion through needles, and the like. The method comprises digestion of the distended intact organ and perfusion of the organ with a carrier medium to remove the islets. Recovery of the islet preparation can then optionally be followed by purification techniques such as size segregation using sedimentation-gradient chromatography.

Accordingly, in one aspect, the invention relates to a method to obtain a subpopulation of cells from a vertebrate organ, which comprises perfusion of the distended, partially digested, organ with a physiologically compatible medium. The carrier medium is recirculated for the perfusion until the desired cell population is dislodged and able to pass through a screen or other size segregation device which retains larger particles. At that time, the recirculation is discontinued and the carrier medium is passed through the organ in an open system to harvest the desired cells.

In the method of the invention, the recirculating perfusion with the carrier medium is conducted with the organ at an elevated temperature of around 28-38° C. to hasten the process, although the preliminary digestion and distention of the organ are conducted at low temperature. At all phases of the process, after passing through the organ, the carrier fluid is cooled to inactivate the collagenase and preserve the cells. In the open circuit phase, the cells are passed into a collector which is also maintained at low temperature.

Thus, the medium is first continuously recirculated through the organ with the organ at elevated temperature but with the carrier medium cooled when not in contact with the organ, as some time is required before the cells appear in the effluent. At such point as the cells appear through the exit screens and the digestion of the organ appears to be optimal, the system is changed from a recirculating to an open system wherein fresh medium is continuously supplied and the effluent containing the harvested subpopulation of desired cells is collected. This is done at low temperature——i.e., the now disintegrating organ, too, is maintained at low temperature of about 4-15° C. for this phase of the process.

In another aspect, the invention relates to an apparatus suitable for carrying out the foregoing process. Both the apparatus and the process are particularly well suited for the preparation of Islets of Langerhans from pancreatic tissue; however, it is also applicable to preparation of hepatocytes from liver, of adipocytes from skin, of splenocytes from spleen, and so forth. Unlike many previous methods, the method is applicable to organs of any vertebrate species, most particularly to mammalian species, and specifically including humans.

BRIEF DESCRIPTION OF THE DRAWINGS

FIGS. 3A, 3B and 3C show micrographs of isolated islets under various conditions.

MODES OF CARRYING OUT THE INVENTION

A. Definitions

Figure 1:
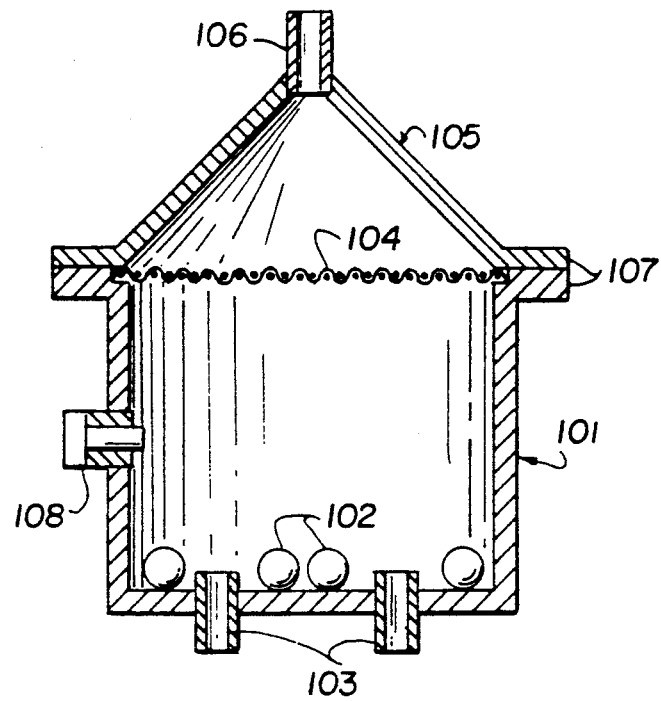
FIG. 1 shows a diagram of one embodiment of the chamber used for perfusion of the intact, distended organ.

As used herein, "physiologically compatible medium" refers to an aqueous buffer at appropriate ionic strength and pH to be compatible with living tissue. The medium may optionally contain supplements such as antibiotics or nutrients such as fetal bovine serum (FBS). Typical media of this type include Hank's solution, Ringer's solution, and the like. The pH and ionic strength conditions can be precisely adjusted in accordance with the organ which is the subject of digestion or perfusion, and the species source of the organ.

"An amount of protease effective to digest" the tissue of the target organ refers to concentrations of collagenase and/or another type of protease, which may in fact be one accompanying putatively "collagenase" enzyme preparations such as trypsin, which concentrations are capable of disrupting the relevant structural protein contained in the organ to an extent sufficient to free the desired subpopulation of cell from entrapment in the organ. As most structural protein comprises collagen, the use of a preparation containing this enzyme is generally a preferred approach by which to obtain the cells in freed form. The concentration needed to be effective is, of course, variable, depending upon the organ and protease preparation used. As an illustration, for freeing Islets of Langerhans from the pancreas, generally speaking 0.5-3, mg/ml of suitable collagenase (see below) is effective. The effective concentration depends on the conditions of digestion, including temperature, pH, and extent of distention; the foregoing suggested amount assumes optimization of these variables. Ascertainment of the amount of "collagenase" needed to be effective in a particular case is well within the ordinary skill of the art, as is determination of effective levels of alternate protease enzyme preparations.

"Collagenase", as commercially available, is sold in various crude preparations of a number of proteases, and the effective level for the invention disclosed herein, of course, depends also upon the nature of the collagenase preparation used. The Sigma Catalog, for example, lists a number of subtypes of the crude preparation which contain varying levels of proteases, such as trypsin, neutral nonspecific protease, and others. In general, "collagenase" is a term used to describe enzyme preparations which are effective in destroying structural proteins, and which actually contain collagenase in substantial amount. Other "protease" preparations, even those lacking in collagenase, can also be used. For example, preparations comprised of trypsin or chymotrypsin are also effective.

"Gentle agitation" is recognized to be a relative term, but it distinguishes the approach of the invention from that previously employed. "Gentle" agitation refers to that sufficient to mix the components of a container without, by virtue of the agitation alone, breaking down the conjugation of physical components. The meaning of this term herein is therefore perhaps best described in contrast to previously described means, such as extrusion through narrow orifices, chopping, blending in a Waring blender, grinding, macerating, and the like.

"Agitation enhancers" refers to blunt, macroscopic objects which are placed in the agitation chamber to increase the mixing encouraged by the agitation, rather than to physically macerate the solid materials.

"Intact" organ refers to an organ in which general disruption of the tissue has not been effected by mechanical means. It may be necessary to divide (cleanly) the organ into 2-3 smaller individual sections in order to accommodate to the size of the equipment or for convenience in handling. Such segregation into intact individual sections leaves the organ within the definition of "intact" herein.

B. General Description of the Invention

The procedure of isolation proceeds generally in the following steps:

First, distention of the intact organ at relatively low temperature by injection or infusion of a collagenase-containing medium;

Second, recirculating the protease-containing medium in a digestion chamber containing the organ while raising the temperature of the medium in the chamber (but cooling the medium when outside the chamber) to permit the effective action of the protease;

Third, monitoring the recirculation to detect the exit of the desired subpopulation of the cells from the intact organ; and Finally, collecting the subpopulation of cells by terminating the recirculation and introducing fresh medium in an open system to circulate past and through the organ and into a collector at a reduced temperature.

The first step (distention) is conducted at a low temperature of approximately 4-28° C. The protease preparation is introduced into the interior of the intact organ and causes the organ to become distended. The organ is preserved at low temperature (4° C.), but the protease preparation injected can be at a higher temperature, typically 24-30° C., or even 37° C. The overall resulting temperature is about 4-28° C. If the organ is the pancreas, the pancreatic duct can be used as a means to conduct protease-containing physiologically compatible medium into the interior; for other organs, e.g., liver, the vascular network can be utilized for the distention. Other methods, such as direct injection, could also be used. The protease preparation is chosen to be suited to the target organ, as is understood in the art. Preferably the protease preparation contains substantial amounts of collagenase. For example, specialized collagenase preparations designed for hepatocyte isolation, pancreatic islet isolation, and adipocyte isolation are available commercially; in general, collagenase preparations vary in the mixture of the specific enzymes they contain, and can be designed for the particular organ which serves as substrate.

When the intact organ is properly distended with the digestion mixture, it is placed into a digestion chamber which permits recirculation of protease-containing medium through and around the organ for conduct of the second (digestion) step. During this process, the temperature in the chamber is elevated to a level sufficient to permit the enzymatic action of the protease, such as collagenase, to increase. Suitable temperatures are in the range of 28–38° C., preferably about 37° C. However, the recirculating fluid is cooled as it leaves the organ to about 5–20° C., and reheated when it reenters the chamber containing the organ. In this way, any cells liberated are preserved from further digestion.

The recirculation is conducted in such a manner that the liberation of the desired cell population from the organ can be monitored. Agitation of the chamber containing the organ is also applied during this process to enhance the liberation of the cells, and the effect of the agitation is enhanced by placing smooth "enhancers" such as marbles in the chamber. The level of agitation can be controlled by altering the characteristics of the agitation enhancers——for example, marbles could be encased in tubing to reduce their mobility.

A preferred embodiment for the digestion chamber component of a recirculation system is shown in FIG. 1. The essential elements are a suitably sized container (chamber), inlet means which permit the recirculating medium to enter the chamber, a screen in front of the exit port which permits the organ or large particles to be retained while the liberated cell subpopulations are permitted to flow through it, and an outlet means for conducting the recirculating medium out of the chamber. The screen regulates the size of the particles exiting the chamber, and a screen is the most convenient filtering device for permitting exit of the cells and retention of the organ. However, other segregation devices such as Velcro, needles or hooks can be used simply to retain the organ in the chamber if size discrimination for the exiting cells is not needed. It is also desirable to have a temperature-monitoring access so that the desirable digestion temperature in the chamber can be maintained.

As shown in FIG. 1, the main, lower chamber 101 is of the proper dimensions to contain the intact organ of interest. It also contains, during the conduct of the process, marbles or other agitation enhancers 102 which aid in the stirring of the medium when the chamber is placed on an agitation device, such as a shaker. The chamber shown in FIG. 1 has two input ports, a and b, shown as 103 in the figure, which permit the recirculating medium (or, later, the fresh medium) to be introduced into the chamber. (Of course, the number of input ports is arbitrary; multiple ports facilitate agitation and mixing, but a single inlet could also be used. In embodiments which use more than one inlet, both recirculating and fresh medium can also be easily introduced simultaneously, if desired.)

In this preferred embodiment, the lower chamber 101 containing the organ is provided with a screen 104 with a pore size appropriate to the subpopulation of cells to be isolated. Typical pore sizes for the isolation of islets from pancreas depend on the species, and are about 190 microns for mouse islets, 230 microns for rat islets, and 280 microns for human islets. The screen shields the outlet means which, in the embodiment in FIG. 1, is a conical upper chamber 105 converging to an outlet port 106. The screen is interchangeable by separating the two portions of the chamber, replacing the screen, and then resealing the chamber by means of the flange portions 107 of the upper and lower chambers. In the embodiment shown in FIG. 1, a thermocouple access 108 is shown which permits monitoring of the temperature.

Figure 2:
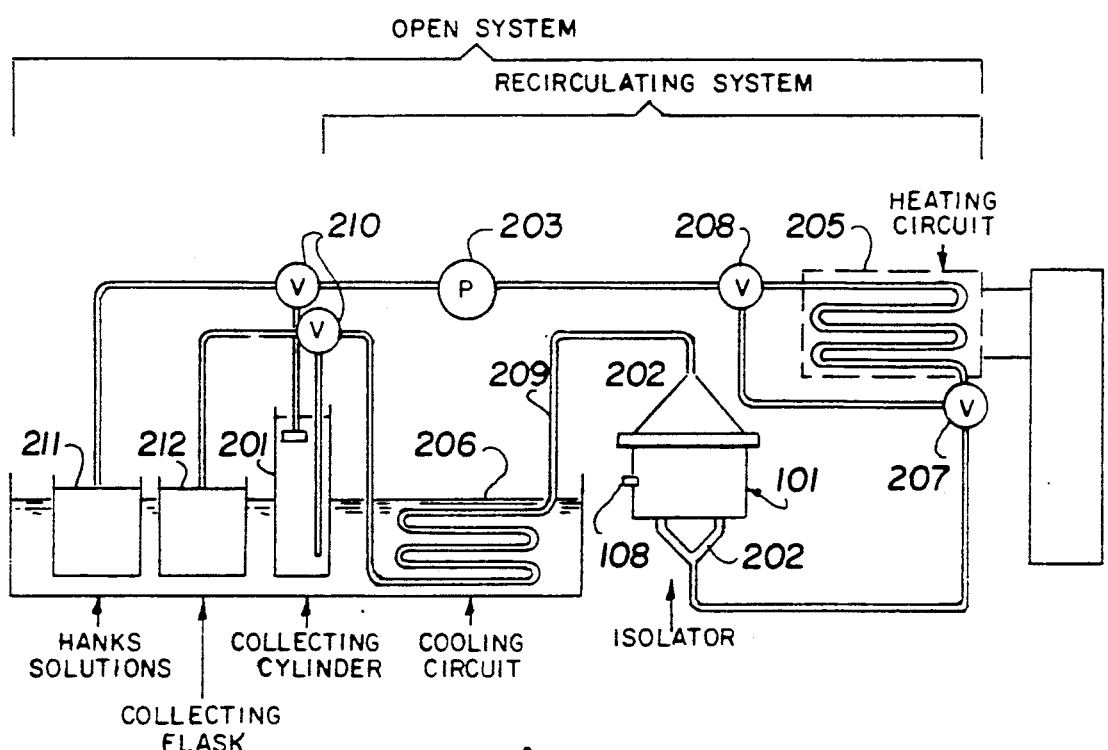
FIG. 2 is a diagramatic representation of the complete system, including the chamber, for separation of the cell subpopulation.

A convenient arrangement of the system as it used to conduct the digestion of the intact organ is shown in FIG. 2. The portion of the diagram designated "Recirculating System" is employed in these primary steps. In the conduct of the recirculation/digestion, the distended organ at low temperature is placed in the chamber 101, and the chamber is filled with additional protease-containing medium. Suitable media include Hand's solution, Ringer's solution, and the like. The temperature is initially maintained at approximately 4–28° C., the screen with pore size suitable for the organ is placed in the chamber, and the chamber is then sealed. The sealed chamber is connected to the recirculation system with connectors 202, and additional medium, optionally containing additional protease, especially collagenase, is pumped through the system using the pump 203. The supply of medium is placed initially in a recirculation supply/collector cylinder 204, to which is added enough medium to supply the entire system. This medium is pumped through the heating circuit 205 and into the "isolator" or digestion chamber 101, as shown. The temperature is monitored at the thermocouple 108. Heating is continued to increase the temperature in the chamber to 28–38° C., preferably ~37° C., at a rate of about 0.5–2° C. per minute.

The exiting medium is circulated through a cooling system 206 which lowers the temperature to about 4° C. to preserve any liberated cells contained in it and then pumped into the recirculating supply/collector cylinder or flask 204, as shown. The recirculation medium continues to be monitored for temperature in the chamber by the thermocouple 108, and when the temperature reaches the desired level, the heating circuit is bypassed, as shown in 207, as necessary. The bypass valve 208 is then used to maintain the proper temperature in the digestion chamber, as verified by the thermocouple at 108.

During the digestion process, the chamber 101 is agitated by placing it on a shaker or by other suitable means to hasten the digestion. However, agitation is not so severe as to destroy the general integrity of the organ. The agitation-enhancing materials inside the chamber aid in mixing the medium inside the chamber and in the release of the desired cell clusters.

Access is provided to the recirculating system through a sampling port 209 so that the presence of cells in the exiting medium can be detected. An essential part of the process is this third step——to monitor the effluent for the presence of the desired cells. Detection is straightforward under ordinary circumstances, as the cells can be seen under a microscope.

The final step in the method of the invention, once the desired cells are detected, is the collection of the cells in fresh medium passed through the disintegrating organ. The temperature of the fresh, nonrecirculating medium, which no longer needs to contain the protease, is in the range of 4–15° C. Sufficient medium at this lowered temperature to wash out the bulk of the cells is employed, and the cell clusters are then harvested by convenient means, such as by mild centrifugation, from the effluent and/or further purified.

Convenient adaption of the preferred apparatus of the invention to this collection step is shown in FIG. 2. When the desired cells are detected in the exit medium, the final, collection step is initiated. The recirculation is halted, and the chamber is placed in an open system for the collection phase, by adjustment of valves 210. During this phase, the temperature is lowered by bypassing the heating circuit and introducing the fresh medium at a temperature of 4-15° C.

The valves at 210 are opened so that the recirculation supply cylinder is bypassed, and the open system is engaged. Fresh physiologically acceptable medium is supplied from the supply chamber 211, bypassing the heating circuit by means of the valve 208, and is passed through the chamber 101 through the cooling circuit 206 and into the collecting flask 212. Depending on the volumes of the supply and collecting flasks 211 and 212, several changes of flask may be necessary during the operation. Collection is continued until cells are no longer being exited from the chamber. The time for each portion of the process varies according to the nature of the organ, the nature of donor, and the specific conditions used for digestion and collection. However, typical times are of the order 20 minutes to over an hour.

It is important to note that in both the recirculation and collecting phases, the cooling circuit serves to inactivate the protease enzyme before the cells reach the collecting tank. Thus, it is only in the chamber that digestion takes place.

When the cells are collected, they can be further purified by any convenient means. One particularly convenient means is by gradient centrifugation, such as Ficoll or Percoll gradients. Other purification methods can, of course, be used, as appropriate to the particular cells being isolated. However, for Islets of Langerhans a particularly important and effective method of purification is Ficoll centrifugation. To conduct this method, the suspensions of cells from the collecting flask(s) are provided with Ficoll gradients and centrifuged to recover the purified fraction containing the islet cells, as is understood in the art.

EXAMPLE

The following examples serve to illustrate but not to limit the invention.

Example 1

A pancreas was removed from a 45-year-old Caucasian male and stored at 4° C. in pH 7 buffer containing 800 mg % glucose. The pancreas was placed in a pan and quickly trimmed to remove fat and connective tissue without removing the outer membrane. The intact pancreas, weighing 126 g, was cut at the neck, and the pancreatic duct was cannulated with an 18 gauge angiocatheter. The organ was then distended by injecting 200 ml of the collagenase solution through the duct. The collagenase was supplied in Hank's solution containing 10% fetal calf serum using 10 mg/ml Sigma Type X collagenase. As the collagenase solution was supplied at room temperature, the temperature of the organ rose to 19° C. The pancreas was again trimmed, removing as much outer membrane as possible, divided into head and tail portions (60 g and 66 g, respectively), and each portion was placed separately in an isolator chamber of the design shown and described in FIG. 1 above. Seven marbles were placed in the bottom of the chamber, then the pancreas portion.

The chamber was then filled with additional collagenase-containing solution, a screen containing pores of 280 micron diameter was placed between the upper and lower chamber, and the isolator chamber was assembled and clamped. The chamber was then placed into the recirculation system shown in FIG. 2.

A total of 50 ml of additional Hank's solution containing 10% fetal bovine serum and antibiotic was placed in the recirculation chamber and the pump was started. Agitation of the chamber was begun; agitation was at first halted for 2 sec out of every 10 until the chamber was free of air. The recirculating solution was passed through the heating element before entering the chamber in such a manner that the temperature rose about 10° C. every two minutes. The temperature of the medium in the chamber was maintained at approximately 34-37° C. for approximately 12 min by suitable manipulation of a bypass valve in front of the heating element until islet cells began to appear in the samples obtained from the sampling port. During this process, the recirculated medium exiting the chamber passed immediately through the cooling element to reduce its temperature to about 4° C. Samples of the cooled effluent were obtained approximately every 2 min, and examined microscopically for the presence of islets. The pancreas could be seen, during this time, visibly to start to digest.

After the islets appeared in the samples, the system was modified to become an open system, and the heating element was permanently bypassed. The pump was turned off, and the leads connecting to the recirculation supply are switched to the supply and collecting flasks 211 and 212 in FIG. 2. Flasks of 400-2,000 ml are used for supply and collection. The pump was restarted, and the fresh Hank's solution from flask 211 (containing 2% FBS and antibiotic and cooled to 4-10° C.) flowed through the chamber carrying the dislodged islets into the collecting flask 212. The islets were collected in a total volume of 1000 ml. A sample of the fluid was counted to establish the number of islets obtained and microscopically examined to ascertain the quality of the islets.

FIG. 3A shows the general appearance of the islets obtained from the head of the pancreas in this procedure; the islets are intact, well-formed cellular masses. Intact islets are present as well as some exocrine pancreas.

The preparation was then subjected to Ficoll separation and reexamined under both high and low magnification as shown in FIGS. 3B and 3C, respectively, to verify that most exocrine pancreas has been removed. The total islet count before Ficoll separation was 402,400, representing 6706 islets per gram of tissue, as ascertained from counts of sampled volumes. A total islet volume of 1.633 ml was obtained in this preparation, calculated based on measurement of the average diameter of the islets and the total number of islets in the preparation. Islet diameters were measured using the micrographs shown in FIGS. 3B and 3C.

Figure 4:
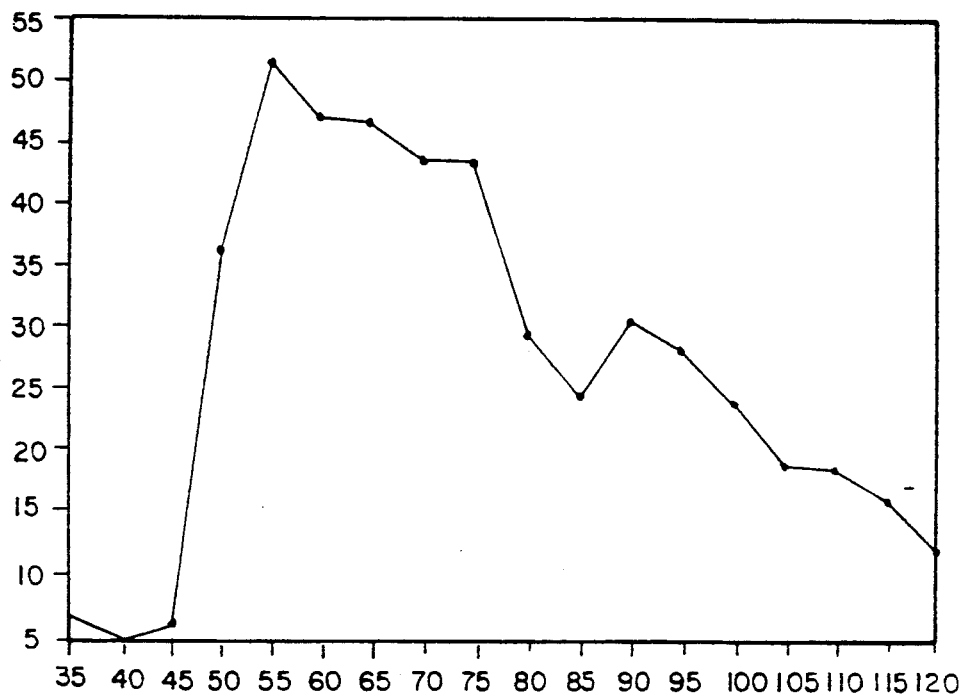
FIG. 4 shows release of insulin from isolated islets upon glucose stimulation.

After Ficoll purification the islets were cultured under standard conditions and their ability to secrete insulin over a 2 hr period, upon stimulation by glucose, was verified, as shown in FIG. 4. A peak secretion rate of over 50 U of insulin was attained after stimulation with glucose for 45 minutes, and there is then a slow decay of secretion to about 15 uU after during the subsequent exposure to low glucose concentration.

Example 2

Using the procedure described in Example 1, five additional pancreases were treated for islet preparation. Table 1 shows the results of these preparations in comparison with that of Example 1. The capacity of these cells to secrete insulin when cultured was verified, and was similar to that of the islets prepared in Example 1.

TABLE 1

| # | AGE | PAN-CREAS wt(g) | Total ISLET #* | ISLETS/g | Total ISLET VOLUME** |
|---|---|---|---|---|---|
| 1 | 24 | 56 | 295,000 | 5,268 | 0.460 ml |
| 2 | 29 | 60 | 311,700 | 5,195 | 0.577 ml |
| 3 | 26 | 58 | 249,600 | 4,303 | 0.684 ml |
| 4 | 27 | 70 | 181,000 | 2,585 | 0.424 ml |
| 5 | 40 | 58 | 459,900 | 7,929 | 1.614 ml |
| 6 | 45 | 60 | 402,400 | 6,706 | 1.633 ml |
| MEAN | | | 316,600 | 5,331 | 0.915 ml |
| SD | | | 101,256 | 1,858 | 0.559 ml |

*Calculated from sample.
**Calculated value based on diameter measurement.

We claim:

1. A method to obtain a designated subpopulation of cells from an intact vertebrate organ, which method comprises, with no more than gentle agitation, the following steps:
   (a) distending the intact organ with a physiologically compatible medium containing an amount of protease effective to free the cells contained in said subpopulation;
   (b) continuously recirculating physiologically compatible medium through and past the distended organ and past a segregation means, which segregation means permits the passage of the cells or clusters thereof of said subpopulation, but not the organ, for a time sufficient to dislodge the cells and cause them to exit the segregation means;
   (c) after the cells commence passage through the segregation means, circulating fresh physiologically compatible medium through and past the organ, and through the segregation means into a collecting means; and
   (d) collecting the subpopulation of cells which pass through the segregation means.

2. The method of claim 1 wherein the organ is the pancreas and the subpopulation of cells is Islets of Langerhans.

3. The method of claim 2 wherein the pancreas is a human pancreas.

4. The method of claim 1 wherein the temperature of the medium in contact with the organ during recirculation in (b) is brought to and maintained at 28-38° C.

5. The method of claim 1 wherein the temperature of the fresh medium in (c) is maintained at 4-15° C.

6. The method of claim 1 wherein the protease is collagenase.

7. The method of claim 1 wherein the organ is distended by cannulation and injection of collagenase-containing medium through the cannula.

8. The method of claim 1 wherein additional protease is added to the organ during the recirculation of (b).

9. The method of claim 1 wherein the segregation means is a filter.

10. The method of claim 9 wherein the pore size of the filter discriminates between the desired cells and larger particles.

11. The method of claim 1 which further includes density separation of the subpopulation of cells obtained in (d).

12. The method of claim 11 wherein the density separation is conducted using Ficoll centrifugation.

13. The method of claim 1 wherein the organ is agitated during the recirculation of (b) and/or the circulating of fresh medium of (c).

14. A method to separate Islets of Langerhans from an intact pancreas which comprises, with no more than gentle agitation, the following steps:
   (a) inserting a cannula into the pancreatic duct and injecting about 50-300 ml of physiologically compatible medium containing about 0.5-3 mg/ml collagenase through the cannula into the pancreas via the duct so as to distend the pancreas;
   (b) placing the distended pancreas into a digestion chamber, which chamber contains physiologically compatible medium having additional collagenase, which medium is of volume sufficient to immerse the pancreas, said chamber having an inlet means and outlet means; the passage of medium through said outlet means being regulated by a size discrimination means which permits the passage of islets, but does not permit the passage of substantially larger particles; and the outlet means being connected to a cooled supply/collector flask;
   (c) continuously recirculating physiologically compatible medium through the chamber with gentle agitation through said inlet and outlet means and through and into said cooled collector, while maintaining the temperature in the chamber at 28-38° C. until islet cells are passed through the outlet means;
   (d) after said islet cells begin to be passed through the outlet means, harvesting the islets obtained by passing fresh physiologically compatible medium through the digestion chamber and through the outlet means into a collector without recirculation.

15. The method of claim 14 wherein the harvest of the islets is conducted at a temperature of 4-15° C.

16. The method of claim 14 wherein the chamber further contains agitation enhancers.

17. The method of claim 16 wherein the agitation enhancers are marbles.

18. The method of claim 14 wherein the physiologically acceptable medium is Hank's solution containing fetal bovine serum.

19. The method of claim 14 wherein the medium used in the process of (a) has a temperature of 24-37° C.

20. The method of claim 14 wherein the pancreas is a human pancreas.

* * * * *